(12) United States Patent  
Devlin et al.

(10) Patent No.: US 7,188,516 B2
(45) Date of Patent: Mar. 13, 2007

(54) FRICTION TESTING APPARATUS

(75) Inventors: Mark Devlin, Richmond, VA (US); Jeremy Senn, Richmond, VA (US)

(73) Assignee: Afton Chemical Corporation, Richmond, VA (US)

( * ) Notice: Subject to any disclaimer, the term of this patent is extended or adjusted under 35 U.S.C. 154(b) by 0 days.

(21) Appl. No.: 11/142,446

(22) Filed: Jun. 2, 2005

(65) Prior Publication Data

US 2006/0272401 A1    Dec. 7, 2006

(51) Int. Cl.
*G01M 13/02*    (2006.01)

(52) U.S. Cl. ......................... 73/119 R; 73/9

(58) Field of Classification Search ............... 73/116, 73/117.2, 118.1, 119 R, 9, 10, 7, 117.3
See application file for complete search history.

(56) References Cited

U.S. PATENT DOCUMENTS

| | | | |
|---|---|---|---|
| 4,023,402 A | 5/1977 | Watanabe | |
| 4,939,922 A * | 7/1990 | Smalley et al. | 73/10 |
| 5,155,664 A | 10/1992 | Holterman et al. | |
| 5,377,525 A | 1/1995 | Hutchinson et al. | |
| 5,679,883 A | 10/1997 | Wedeven | |
| 6,167,745 B1 | 1/2001 | Hamer et al. | |
| 7,000,451 B1 * | 2/2006 | Wegand et al. | 73/9 |

OTHER PUBLICATIONS

Presentation made before Ford Motor Company on Jun. 3, 2004. "Limited Slip Axle Shudder: Root Cause Investigation"

* cited by examiner

*Primary Examiner*—Eric S. McCall
(74) *Attorney, Agent, or Firm*—Luedeka, Neely & Graham PC

(57) ABSTRACT

A testing apparatus for measuring the friction characteristics between two components in rolling or sliding contact with one another is disclosed herein. The testing apparatus includes a traction surface, a first support structure adapted to support the traction surface while allowing for rotation of the traction surface, and a drive mechanism to rotate the traction surface. The testing apparatus further includes a movable second support structure proximate to the first support structure and adapted to move a test material into contact with the traction surface. An attachment piece is mechanically fixed to the movable second support structure. The attachment piece is constructed to receive and hold the test material relative to the traction surface. The testing apparatus also includes a force measuring device adapted to measure the frictional forces produced between the test material and the traction surface.

22 Claims, 4 Drawing Sheets

FRICTION TESTING APPARATUS

BACKGROUND OF THE INVENTION

1. Field of the Invention

This invention relates to a testing apparatus and, in particular, to an attachment for an apparatus for testing the frictional forces between two materials.

2. Background Art

Conventional clutch plates are composite materials formed by adhering a friction material to a steel plate. For purposes of warranty protection, among other reasons, manufacturers must be able to test and evaluate the durability and life-span of the clutch plates. Therefore, manufacturers must be able to test and measure the friction characteristics of the clutch plates. Further, when a system fails after use, the aged clutch plate must be tested and evaluated in order to determine the reason for failure.

A number of testing apparatuses have been proposed to test the friction and/or traction forces between two or more materials in rolling or sliding contact with each other. One such an apparatus is disclosed in U.S. Pat. No. 6,167,745, hereby incorporated by reference in its entirety. Such a device is designed to measure the rolling traction and/or friction between a friction material (or friction surface) and a second friction surface. Devices are also known to test and measure the friction between two steel components. In order to test the friction characteristics of composite materials such as clutch plates, a portion of the friction material is typically tested before the material is adhered to the steel plate. This testing process neglects the fact that the later-performed adhesion of the friction material to the steel plate affects the friction properties of the friction materials. Further, failure testing of aged clutch plates is not possible with currently known devices, because the friction material cannot be tested while attached to the steel plate in existing devices.

There exists a need for a testing device which can test an actual clutch or gear piece and give an accurate measurement of the friction properties of composite materials.

BRIEF SUMMARY OF THE INVENTION

Disclosed herein is a testing apparatus for measuring the friction and/or traction characteristics between two materials in rolling or sliding contact with one another. The testing apparatus includes a traction surface, a first support structure adapted to support the traction surface while allowing for rotation of the traction surface, a drive shaft coupled to the traction surface, and a power source coupled to the drive shaft and adapted to rotate the drive shaft and thereby rotate the traction surface. The testing apparatus further includes a movable second support structure proximate to the first support structure and adapted to move a test material into contact with the traction surface. An attachment piece is mechanically fixed to the movable second support structure. The attachment piece is constructed to receive and hold the test material relative to the traction surface. The testing apparatus also includes a force measuring device coupled to either the first support structure or the movable second support structure. The force measuring device is adapted to measure the frictional forces produced between the test material and the traction surface when the test material is in contact with the traction surface and the traction surface is rotated by the drive shaft. Disclosed herein are also methods of using such a testing apparatus.

BRIEF DESCRIPTION OF THE FIGURES

Embodiments of a testing apparatus and method of use will now be described with reference to the accompanying drawings in which.

DETAILED DESCRIPTION OF THE INVENTION

While specific configurations and arrangements of a testing apparatus and methods of use are discussed herein, it should be understood that this is done for illustrative purposes only. A person skilled in the relevant art will recognize that other configurations and arrangements can be used without departing from the spirit and the scope of the appended claims.

Figure 1:
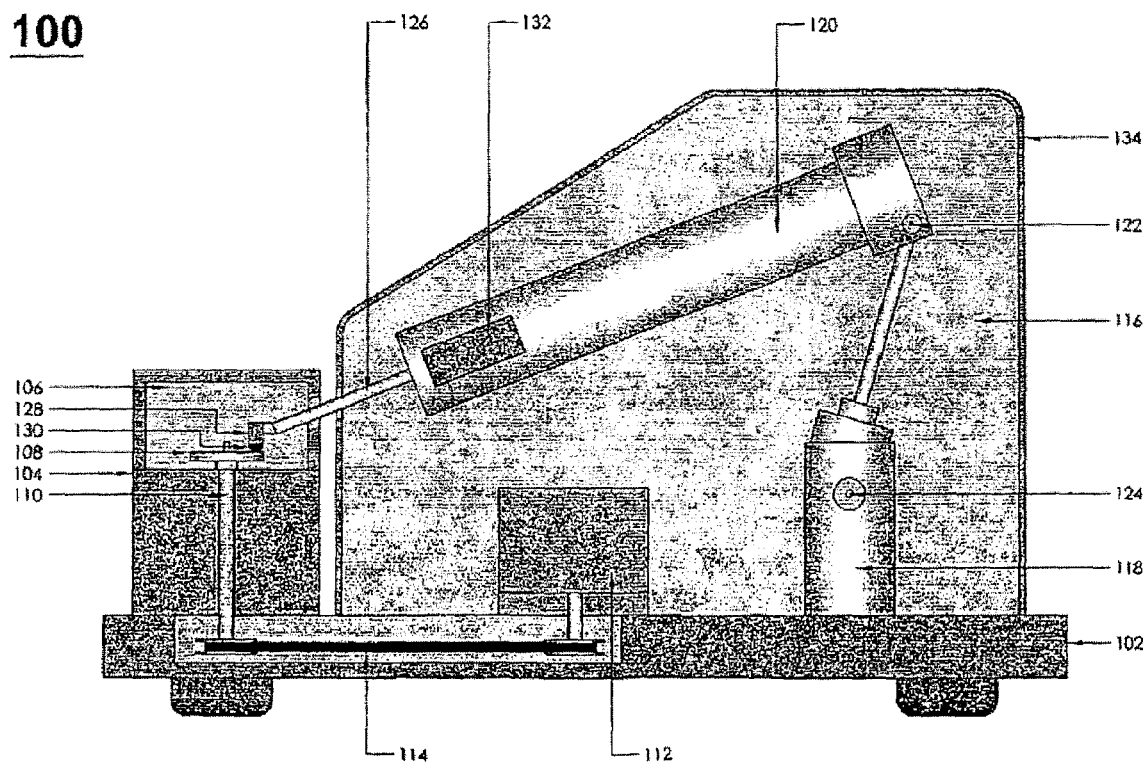
FIG. 1 shows a schematic view of a testing apparatus.

FIG. 1 shows a schematic view of the testing apparatus 100. A similar testing apparatus is disclosed in the above-referenced U.S. Pat. No. 6,167,745. Testing apparatus 100 includes a base portion 102. Mounted on the base portion 102, is a first support structure, or testing chamber 104. Testing chamber 104 includes a reservoir 106, wherein a testing surface, or traction surface 108 is rotatably disposed. Traction surface 108 is preferably a disc with a planar surface.

Traction surface 108 is coupled to a drive shaft 110. Drive shaft 110 is coupled to a drive mechanism 112. Drive mechanism 112 is preferably a DC servo motor, but alternatively can be any power source or drive means known in the art. Drive mechanism 112 and drive shaft 110 are coupled through a belt-pulley combination 114.

Mounted on base 102 is a second support structure 116. Second support structure 116 includes a stepper motor 118 and an extension arm 120. Linkage joints 122 and 124 further serve as means for allowing for movement of extension arm 120. Actuation of stepper motor 118 controls the movement and displacement of extension arm 120.

In one embodiment, a force measuring device 132 is coupled to the extension arm 120. Alternatively, a force measuring device can be coupled directly to the traction surface 108. Force measuring device 132 is adapted to measure the frictional forces produced when a testing material 130 is brought into contact with the traction surface 108 and the traction surface 108 is rotated by the drive mechanism 112. Force measuring device 132 measures the frictional forces produced by measuring the elastic deformation of the system.

Extension arm 120 includes an outward extending portion 126, which extends into reservoir 106 of testing chamber 104. Fixed to outward extending portion 126 is an attachment piece 128. Attachment piece 128 is adapted to receive and hold testing material 130.

Testing apparatus 100 also includes a cover 134 to protect the system components.

Figure 2:
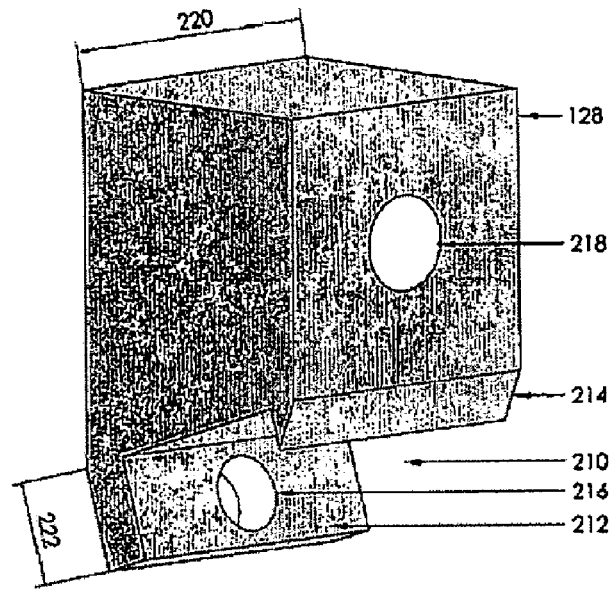
FIG. 2 shows a perspective view of a clutch plate mounting device.

FIG. 2 is a schematic view of attachment piece 128. As shown in FIG. 2, attachment piece 128 is a cube-like device including a U-shaped cavity, or U-shaped section 210. The U-shaped section 210 is adapted to receive and hold testing material 130. U-shaped section 210 is generally formed of extensions, or lips 212 and 214. Extensions 212 and 214 act as lip portions, which interlock and hold testing material 130 within the U-shape section 210 of attachment piece 128. Attachment piece 128 may be formed from an aluminum cube for ease of manufacture, but may also be formed of other materials, such as steel. U-shaped section 210 can be formed by manufacturing techniques known in the art.

Figure 3:
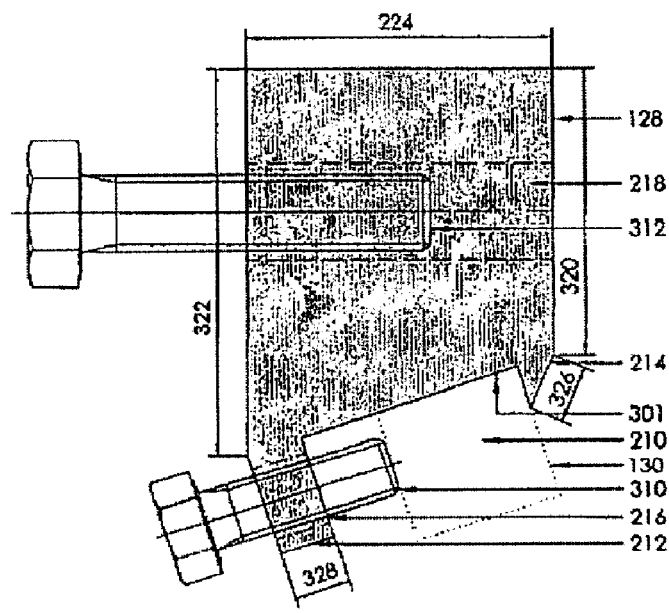
FIG. 3 shows a side view of the clutch plate mounting device of FIG. 2.

FIG. 3 shows a side view of the attachment piece 128. Extensions 212 and 214 extend from the attachment piece 128 and form angles of ninety degrees or less with the bottom surface 301 of the attachment piece 128. A screw hole 216 is formed through one of the lip portions, preferably extension 212. Screw hole 216 transects through extension 212. A set screw 310 is inserted through screw hole 216 to thereby interlock with testing material 130 and hold testing material 130 within U-shaped section 210 of attachment piece 128.

A screw hole 218 intersects through the upper portion of attachment piece 128. A screw 312 is inserted through screw hole 218 to thereby mechanically fix attachment piece 128 to outward extending section 126.

Testing material 130 can be a piece of an actual clutch plate, or gear. For example, a piece of a clutch plate can be cut from a new or aged clutch plate. The piece of the clutch plate is then inserted into U-shaped section 210, and set into place with set screw 310. As such, attachment piece 128 serves as a clutch plate mounting device. When attachment piece 128 is fixed to outward extending section 126, the piece of the clutch plate can be brought into contact with the testing or traction surface 108. As such, a more accurate measure of the friction characteristics of the actual clutch plate can be measured because the friction material is being tested while adhered to the steel plate.

In operation, reservoir 106 is filled with a testing fluid such as a lubricant or operational oil. Testing chamber 104 includes cooling or heating means used to simulate operational temperatures. Drive mechanism 112 is actuated to rotate traction surface 108. Second support structure 116 is actuated and adjusted to bring test material 130 into contact with traction surface 108. When test material 130 is in contact with the rotating traction surface 108, a frictional force is produced, which simulates the frictional force produced in actual operation of the clutch plates. The frictional forces are measured by force measuring device 132.

As such, testing apparatus 100 allows for the accurate testing of clutch plates or gear components because attachment piece 128 provides a means of holding an actual piece of the clutch or gear to be tested. Other known devices allowed for the testing of the friction material which was later adhered to a steel component to form a clutch plate or gear. Such devices did not take into account the changes in the frictional properties of the friction material during the adhesion process. Further, once a clutch plate has been used, it is difficult, if not impossible, to remove the aged friction material for testing. With the testing apparatus 100 described herein, a piece of the aged clutch plate can be cut and set in attachment piece 128, and thereafter tested. This testing technique provides a means of testing and evaluating the reasons for failure in an aged clutch plate that has been taken from a system that failed in operation. Further, tests can be performed with aged lubricant and new clutch plates to determine if the cause of failure is the aged lubricant rather than the aged clutch plate.

In an exemplary embodiment, attachment piece 128 has the following dimensions. Screw hole 218 has a diameter of 0.41 inches. Screw hole 216 has a diameter of 0.31 inches. Distance 320 is 1.17 inches. Distance 322 is 1.57 inches. Distance 224 is 1.25 inches. Distance 220 is 1.25 inches. Distance 222 is 0.44 inches. Distance 326 is 0.23 inches. Distance 328 is 0.23 inches.

Figure 4:
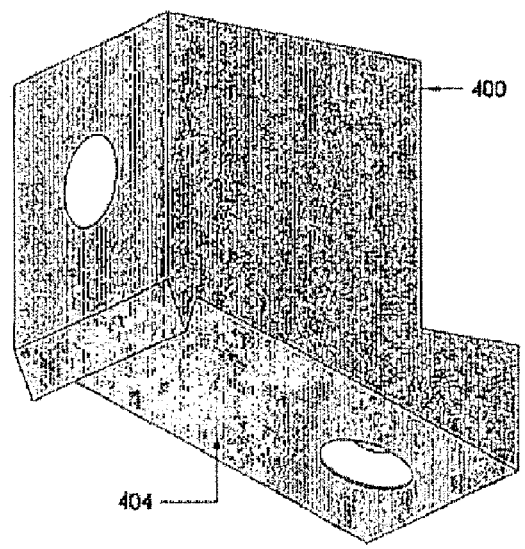
FIG. 4 shows a perspective view of an alternative clutch plate mounting device.

FIG. 4 shows a perspective view of an alternative clutch plate mounting device, or attachment piece 400. Attachment piece 400 uses a bevel-head set screw 402 to interlock and secure test material 130 to the bottom surface 404 of attachment piece 400. To secure test material 130 to the bottom surface 404 of the attachment piece 400, test material 130 is press fit to the bottom surface 404 by the bevel-head portion of set screw 402.

Figure 5:
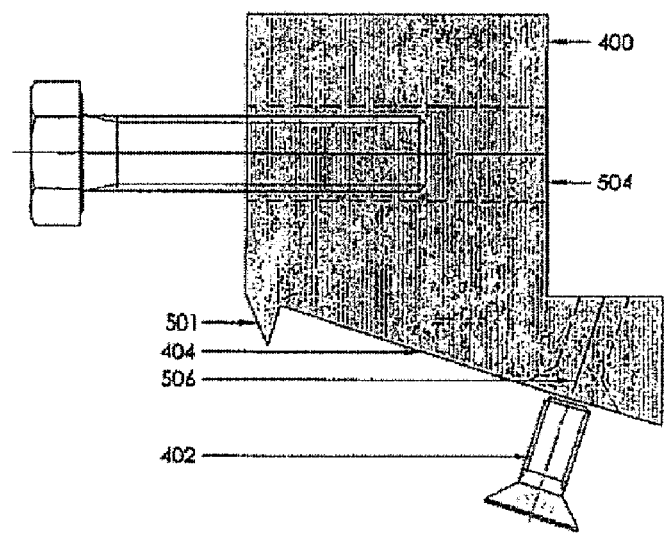
FIG. 5 shows a side view of the clutch plate mounting device of FIG. 4.

FIG. 5 shows a side view of the attachment piece 400 of FIG. 4. Attachment piece 400 includes a lip portion 501, which forms an acute angle with the bottom surface 404 of attachment piece 400. Lip portion 501 serves to aid in the setting and securing of test material 130 to attachment piece 400. Attachment piece 400 further includes screw hole 504, which transects through the attachment piece 400 and is used to set and secure the attachment piece 400 to second support structure 116. A screw hole 506 is disposed through the bottom surface 404 of attachment piece 400 to screw bevel-head set screw 402 into the attachment piece 400.

Figure 6:
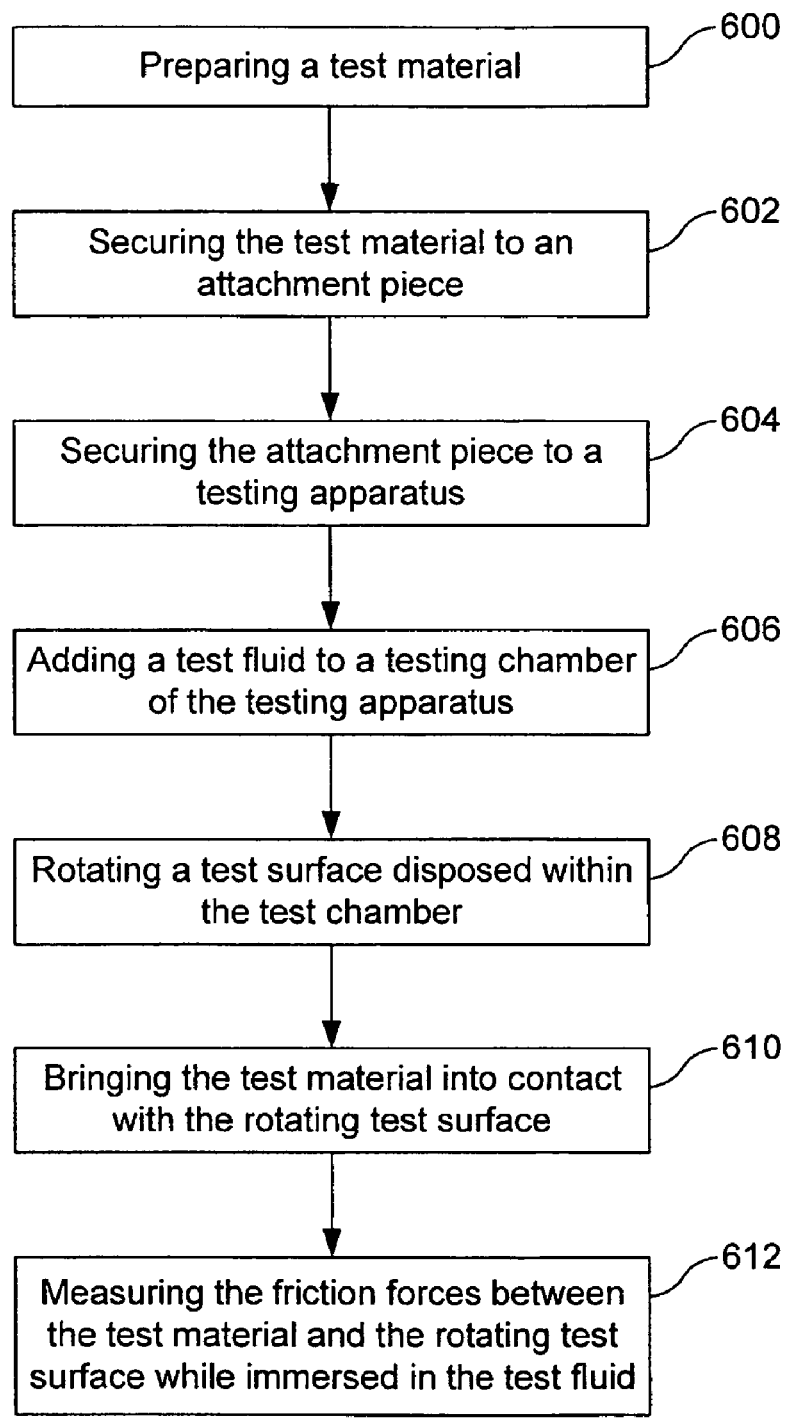
FIG. 6 is a flow chart illustrating a method of testing the friction forces between at least two materials.

FIG. 6 is a flow chart illustrating a method of testing the friction forces between at least two materials. In step 600, a test material is prepared. Generally, the test material is prepared by cutting out a piece of a clutch plate, such as an aged clutch plate, for testing. In step 602, the test material is secured to an attachment piece. The attachment piece may be a clutch mounting device as described in the above embodiments. In step 604, the attachment piece is secured to a testing apparatus, such as the one described above. In step 606, a test fluid, such as a lubricant, engine oil, or automatic transmission fluid, is added to a test chamber of the testing apparatus. In step 608, a test surface disposed within the testing chamber is rotated through a drive mechanism. Steps 602, 604, 606 and 608 may be performed in any order. In step 610, the test material is brought into contact with the test surface. Finally, in step 612, the friction forces between the test material and the rotating test surface are measured while the test material and test surface are immersed in the test fluid.

Example embodiments of a testing apparatus and method of use have been described herein. These example embodiments have been described for illustrative purposes only, and are not limiting. Other embodiments are possible and are covered by the appended claims. Such embodiments will be apparent to persons skilled in the relevant art(s) based on the teachings contained herein.

What is claimed is:

1. A testing apparatus comprising:
    a traction surface;
    a first support structure adapted to support the traction surface while allowing for rotation of the traction surface;
    a drive shaft coupled to the traction surface;
    a power source coupled to the drive shaft and adapted to rotate the drive shaft and thereby rotate the traction surface;
    a movable second support structure proximate to the first support structure and adapted to move a test material into contact with the traction surface;
    an attachment piece mechanically fixed to the movable second support structure, wherein the attachment piece is constructed to receive and hold the test material relative to the traction surface, where the test material is rigidly held against and does not rotate with the rotating traction surface; and a force measuring device coupled to either the first support structure or the movable second support structure and adapted to measure the frictional forces produced between the test material and the traction surface when the test material is in contact with the traction surface and the traction surface is rotated by the drive shaft.

2. A testing apparatus as defined in claim 1, wherein the attachment piece includes a set screw which interlocks with the test material to thereby hold the test material in the attachment piece.

3. A testing apparatus as defined in claim 2, wherein the set screw is a bevel-head screw.

4. A testing apparatus as defined in claim 1, wherein the testing material is a portion of a clutch plate and the attachment piece is a clutch plate mounting device.

5. A testing apparatus as defined in claim 1, wherein the attachment piece includes a lip portion which interlocks with the test material to thereby hold the test material in the attachment piece.

6. A testing apparatus as defined in claim 1, wherein the attachment piece takes on a cube-like structure and includes a U-shaped section adapted to receive the test material.

7. A testing apparatus comprising:
a base;
a testing chamber mounted on the base;
a testing surface rotatably disposed within the testing chamber;
a drive mechanism extending into the testing chamber and coupled to the testing surface, wherein the drive mechanism is adapted to rotate the testing surface;
a movable support structure mounted on the base;
an attachment piece fixed to an end of the movable support structure, wherein the attachment piece is adapted to receive and hold a test material, where the test material is rigidly held against and does not rotate with the rotating testing surface; and
a force measuring device adapted to measure the frictional force produced between the testing surface and the testing material when the testing surface is rotated by the drive mechanism and the testing material is brought into contact with the testing surface by movement of the movable support structure.

8. A testing apparatus as defined in claim 7, wherein the testing chamber includes a testing fluid and wherein the force measuring device is adapted to measure frictional characteristics of the test material and the test fluid.

9. A testing apparatus as defined in claim 7, wherein the attachment piece is a clutch plate mounting device and the test material is a portion of a clutch plate.

10. A testing apparatus as defined in claim 7, wherein the attachment piece includes a set screw adapted to interlock with the test material and thereby hold the test material relative to the attachment piece.

11. A testing apparatus as defined in claim 10, wherein the set screw is a bevel-head screw.

12. A testing apparatus as defined in claim 7, wherein the attachment piece includes a lip portion adapted to hold the test material within the attachment piece.

13. A testing apparatus as defined in claim 7, wherein the attachment piece takes on a cube-like structure and includes a U-shaped section adapted to receive the test material.

14. A testing apparatus as defined in claim 7, wherein the attachment piece includes a bottom surface having a screw hole therein.

15. A testing apparatus as defined in claim 14, wherein the attachment piece includes a lip portion which forms an acute angle with the bottom surface of the attachment piece.

16. A method of measuring the friction forces between at least two materials comprising:
(a) securing a test material to an attachment piece;
(b) securing the attachment piece to a testing apparatus which includes a force measuring device;
(c) rotating a test surface disposed within a testing chamber of the testing apparatus;
(d) bringing the test material into contact with the rotating test surface, where the test material is rigidly held against and does not rotate with the rotating test surface; and
(e) measuring the friction forces between the test material and the rotating testing surface with the force measuring device.

17. A method as defined in claim 16, wherein step (a) includes securing the test material to the attachment piece by interlocking the test material with a set screw which screws into the attachment piece.

18. A method as defined in claim 16, further including adding a testing fluid to the testing chamber such that step (e) includes measuring the friction forces between the test material and the rotating test surface while immersed in the testing fluid.

19. A method as defined in claim 18, wherein the testing fluid is an automatic transmission fluid.

20. A method as defined in claim 18, wherein the testing fluid is an engine oil.

21. A method of measuring the friction characteristics of an aged clutch plate comprising:
(a) cutting out a piece of an aged clutch plate;
(b) securing the piece of the aged clutch plate to an attachment piece, wherein the attachment piece is fixed to a support structure of a testing apparatus;
(c) rotating a testing surface which is mounted on a second support structure of the testing apparatus;
(d) bringing the piece of the aged clutch plate into contact with the rotating testing surface, where the piece of the aged clutch plate is rigidly held against and does not rotate with the rotating testing surface; and
(e) measuring the friction forces produced between the piece of aged clutch plate and the rotating testing surface.

22. A method as defined in claim 19, wherein step (d) includes bringing the piece of aged clutch plate into contact with the testing surface within a testing chamber of the testing apparatus, wherein the testing chamber includes a testing fluid such that the friction forces produced between the piece of aged clutch plate and the rotating testing surface are measured while immersed in the testing fluid.

* * * * *